United States Patent [19]

Mattson

[11] 4,034,083
[45] July 5, 1977

[54] COMPOSITIONS FOR INHIBITING ABSORPTION OF CHOLESTEROL

[75] Inventor: Fred Hugh Mattson, Cincinnati, Ohio

[73] Assignee: The Procter & Gamble Company, Cincinnati, Ohio

[22] Filed: Nov. 3, 1975

[21] Appl. No.: 628,265

[52] U.S. Cl. .............................. 424/180; 424/236; 424/237; 424/284; 424/311; 424/312; 424/331; 424/344

[51] Int. Cl.² ................ A61K 31/70; A61K 31/22; A61K 31/23

[58] Field of Search .......... 424/180, 312, 311, 236, 424/237, 284, 331, 344

[56] References Cited

UNITED STATES PATENTS 3,351,531  11/1967  Noznick et al. ............... 424/236

*Primary Examiner*—Sam Rosen
*Attorney, Agent, or Firm*—Rose Ann Dabek; Jerry J. Yetter; Richard C. Witte

[57] ABSTRACT

Polyol fatty acid polyesters having at least four fatty acid ester groups are fortified with fat-soluble vitamins and used in pharmaceutical compositions for treating and/or preventing hypercholesterolemia in animals, especially humans, and in low-calorie foods.

23 Claims, No Drawings

COMPOSITIONS FOR INHIBITING ABSORPTION OF CHOLESTEROL

BACKGROUND OF THE INVENTION

The present invention relates to certain edible, but non-absorbable and non-digestible, polyesters which can be used as fat substitutes in foods and as pharmaceutical compositions. The polyesters herein interfere with the body's absorption of cholesterol and thereby provide a means for treating hypercholesterolemia. It has now been found that these polyesters, while effective for their intended purpose, can undesirably interfere with the body's source of fat-soluble vitamins. By the present invention, the polyesters are fortified with fat-soluble vitamins, thereby avoiding this undesirable effect.

High blood cholesterol (hypercholesterolemia) is recognized as being a risk factor in cardiovascular disease which comprises a major health care problem, today. Epidemiological studies have demonstrated that, with few exceptions, populations consuming large quantities of saturated fat and cholesterol have a relatively high concentration of serum cholesterol and a high mortality rate from coronary heart disease. While it is recognized that other factors can also contribute to the development of cardiovascular disease, there appears to be a causal relationship between the concentration of serum cholesterol, in which hypercholesterolemia results in the accumulation of undesirable amounts of cholesterol in various parts of the circulatory system (arteriosclerosis) or in soft tissues (xanthomatosis), and coronary disease and coronary mortality rates.

A variety of dietary and drug regimens have been suggested for alleviating or preventing hypercholesterolemia.

By providing a fat substitute which is non-absorbable and non-digestible, the total content of cholesterol in the body can be lowered. Mineral oil has been suggested both as a fat substitute and as a kind of "intestinal solvent" to dissolve cholesterol and cause its removal in body wastes. However, mineral oil has never been accepted for these uses. Moreover, mineral oil is partially absorbed and undesirably deposits in the liver.

In the present invention, non-absorbable, non-digestible polyesters of sugars (or sugar alcohols) are used as fat substitutes in foods and in unit dose forms as therapeutic compositions. The polyesters herein are fat-like in their physical properties and are excellent fat substitutes for use in foods. Moreover, the sugar polyesters herein efficiently inhibit absorption of cholesterol by the body and, in contrast with mineral oil, are not absorbed and/or deposited in the liver during usage in a treatment/prevention regimen with persons having or likely to develop hypercholesterolemia.

It has now been determined that ingestion of the sugar polyesters herein can interfere with the body's uptake of fat-soluble vitamins. It has also been found that this problem can be overcome by fortifying the polyesters herein, or foods containing said polyesters, with fat-soluble vitamins.

PRIOR ART

U.S. Pat. No. 1,656,474 (1928) to Dubin discloses edible fat compositions consisting of ethyl and glycerol esters of odd chain fatty acids in combination with fat-soluble vitamins.

U.S. Pat. No. 3,600,186 (1971) to Mattson discloses low calorie food compositions containing polyol polyesters of the type employed herein. In a fat balance experiment, the diet fed to animals contained water-soluble vitamins, but there is no mention of fat-soluble vitamins in the polyester component of this diet.

Mattson and Nolen, *The Journal of Nutrition* Vol. 102, No. 9, Sept. 1972, at pages 1171-1175, report on the lack of absorbability of sugar polyesters of the type employed herein in rats. The rats were fed water-soluble vitamins in the diet and given one drop of fat-soluble vitamins per week.

Fallet, Glueck, Mattson and Lutmer, *Clinical Research* XXIII No. 3 pages 319A (1975) report the lowering of both serum cholesterol and vitamin A levels in subjects receiving sugar polyesters of the present type.

U.S. Pat. No. 2,962,419 (1960) to Minich relates to neopentyl fatty esters, their use as fat substitutes, and their use with "vitamins", among other things. Fat-soluble vitamins do not appear to be specifically contemplated in the Minich disclosure.

U.S. Pat. No. 3,160,565 (1964) to H. E. Duell relates to sugar mono-, di- and tri-esters and their use as carriers for various orally-administered medicinals, including the B vitamins.

U.S. Pat. No. 3,849,554 (1974) to Winitz discloses means for reducing blood serum cholesterol by ingesting diets comprising a fatty acid source, said diets being low in sucrose.

U.S. Pat. No. 2,893,990 (1959) to Hass, et al., discloses fatty acid mono- and di-esters of sucrose which aid in the absorption of fat from the digestive tract.

U.S. Pat. No. 3,158,490 (1964) to Baur and Lutton discloses non-cloudy salad oils containing esters of disaccharides in which there are not more than five unesterified hydroxy groups. See also U.S. Pat. Nos. 5,059,009 (1962) and 3,059,010 (1962) to Schmid and Baur.

U.S. Pat. No. 2,997,492 (1961) to Martin is directed to a method of making partial fatty acid esters of hexitols. U.S. Pat. No. 2,997,491 (1961) to Huber is directed to the synthesis of partial fatty esters of inositol. The general methods of synthesis disclosed in these patents can be used to prepare the polyesters herein. Preferred methods of synthesis are fully disclosed hereinafter.

The copending application of Mattson and Volpenhein, entitled PHARMACEUTICAL COMPOSITIONS FOR INHIBITING ABSORPTION OF CHOLESTEROL, Ser. No. 425,010, filed Dec. 14, 1973, now U.S. Pat. No. 3,954,976 discloses and claims sugar polyesters of the type employed herein for the treatment and/or prevention of hypercholesterolemia. The use of these polyesters in combination with fat-soluble vitamins in the manner of the present invention is not disclosed.

In addition to the foregoing, there are other patents directed to the use of fat-soluble vitamins in a variety of naturally-occurring oils not contemplated by the present invention. See, for example, U.S. Pat. No. 2,685,517, issued Aug. 3, 1954, to Nutrition Products, Inc.

SUMMARY OF THE INVENTION

The present invention is based on the discovery that administration of an anti-hypercholesterolemic dose of a polyester of the type described herein to an animal (especially humans) afflicted with or susceptible to hypercholesterolemia can interfere with normal absorption of fat-soluble vitamins in said animal. By fortifying the polyester material with fat-soluble vitamins, this undesirable effect is overcome.

The present invention encompasses compositions of matter which comprise a non-absorbable, non-digestible polyol fatty acid polyester of the type described hereinafter and sufficient fat-soluble vitamins selected from the group consisting of vitamin A, vitamin D, vitamin E and vitamin K, or mixture thereof, to prevent abnormally low tissue levels of any of said fat-soluble vitamins in animals ingesting said compositions. The compositions can be used as fat substitutes in cooking or can be self-administered to reduce the body's cholesterol level. Such compositions also find use as stool softening laxatives.

The present invention also encompasses pharmaceutical compositions in effective unit dosage amounts for inhibiting the absorption of cholesterol without altering the body's level of fat-soluble vitamins, said compositions comprising from about 1 gram to about 5 grams of the polyol polyesters herein and sufficient fat-soluble vitamins, or mixtures thereof, to prevent abnormally low levels of any of said fat-soluble vitamins in humans ingesting said compositions.

The polyester materials herein are non-absorbable and non-digestible and are suitable for use in low calorie fat-containing food compositions. Accordingly, the present invention also encompasses low calorie fat-containing food compositions comprising non-fat ingredients and fat ingredients wherein from about 10% to about 100% of the total fat ingredients comprise non-absorbable, non-digestible polyol fatty acid polyesters of the type disclosed hereinafter, said food compositions being fortified with sufficient fat-soluble vitamin, or mixtures thereof, over and above that naturally present in said food compositions, to prevent abnormally low levels of any of said fat-soluble vitamins in humans ingesting said compositions.

The present invention also encompasses methods for inhibiting the absorption of cholesterol without decreasing the tissues' supply of fat-soluble vitamins comprising systemically (generally, orally) administering to animals susceptible to or afflicted with hypercholesterolemia successive therapeutically effective doses of the polyesters herein and sufficient fat-soluble vitamins to prevent abnormally low levels of said vitamins from developing in said animals.

DETAILED DESCRIPTION OF THE INVENTION

The consumption of diets containing sucrose polyesters (SPE) has been shown to result in the desirable decrease in absorption of dietary cholesterol in animals; see Mattson, Jandacek and Glueck, Clinical Research 23 445A (1975).

The following is a brief description of animal studies whereby the effect of the ingestion of the non-absorbable, non-digestible sucrose polyesters herein on vitamin A (an oil-soluble vitamin) uptake in rats was first determined.

In general terms, the animal studies involved feeding groups of rats of vitamin A-free diet for seven days. During this time, the animals were fed either cottonseed oil (CSO) or SPE, or mixtures of the two, as the sole source of fats in the diet. (The SPE is described in more detail hereinafter).

After the initial seven-day period, the diets of the animals were supplemented with vitamin A. Following the seven days on the diets containing vitamin A, the animals were sacrificed and their livers were removed and analyzed for vitamin A content by the Carr-Price method, using the procedure of Ames, Risley and Harris.

In studies of the foregoing type the marked differences of the response of the animals to the type of dietary fat ingested was unequivocal. Thus, when the dietary fat was CSO, over 70% of the vitamin A that was consumed was stored in the liver. The complete replacement of the normal dietary fats with SPE resulted in the storage of less than 10% of the vitamin A that was consumed.

In light of studies of the foregoing type, it is possible to provide a picture of the effect of SPE on fat-soluble vitamin (and cholesterol) uptake by the individual. Under usual dietary conditions (i.e., when ingesting ordinary absorbable, digestible oils or fats such as CSO), vitamin A, like cholesterol, initially is dissolved in an oil phase of triglycerides in the lumen of the intestinal tract. A portion of the triglycerides is hydrolyzed to monoglycerides and free fatty acids which, together with bile salts, form a micellar phase. Vitamin A is then distributed between the oil phase of unhydrolyzed triglyceride and the micellar phase. The proportion of vitamin A in each will be a function of the volume of each phase and the distribution coefficient of the vitamin. Eventually, almost all of the triglycerides are hydrolyzed and a major portion of the vitamin is absorbed.

In contrast, SPE and triglycerides are miscible. When both are present, a single oil phase is formed. The digestion products of the triglycerides enter the micellar phase but SPE, because it is not hydrolzyed, remains as an oil phase. A significant portion of the ingested vitamin A (and cholesterol) remains in this SPE oil phase, the amount again depending on the volumes of the SPE oil and micellar phases and the distribution coefficient of the vitamin. When the SPE is discharged, unchanged, in the stools, the oil-soluble vitamin A dissolved in the SPE is also lost. A similar sequence of events presumably occurs also in the case of vitamin E and also with the other fat-soluble vitamins, D and K.

As can be seen from the foregoing, the physicochemical properties which make the SPE so useful in preventing uptake of cholesterol by the body are the self-same properties which undesirably interfere with uptake of fat-soluble vitamins.

This type of interference with the absorption of vitamins A and E has been demonstrated in human volunteers who consumed SPE. The consequence of SPE ingestion was a drop in the blood (plasma) levels of these vitamins.

By the present invention SPE-type polyesters are fortified with fat-soluble vitamins, especially vitamin A, vitamin E and vitamin D, and mixtures thereof. (The polyesters can also be fortified with vitamin K. However, since the body can synthesize vitamin K, supplementation of the polyesters therewith is probably not critical to adequate nutrition in the normal subject). The vitamin-fortified polyesters are used as fat substitutes in foods, in unit dose forms as pharmaceutical compositions, or are provided in bulk form for self-administration in a therapeutic or dietetic regimen.

The non-absorbable, non-digestible polyesters and fat-soluble vitamins employed herein and foodstuffs, therapeutic compositions, and the like, comprising vitamin-fortified polyesters are described in detail hereinafter.

The polyol polyesters (or, simply, polyesters) employed in this invention comprise certain polyols, especially sugars or sugar alcohols, esterified with at least four fatty acid groups. Accordingly, the polyol starting material must have at least four esterifiable hydroxyl groups, Examples of preferred polyols are sugars, including monosaccharides and disaccharides, and sugar alcohols. Examples of monosaccharides containing four hydroxyl groups are xylose and arabinose and the sugar alcohol derived from xylose, which has five hydroxyl groups, i.e., xylitol. (The monosaccharide, erythrose, is not suitable in the practice of this invention since it only contains three hydroxyl groups; but the sugar alcohol derived from erythrose, i.e., erythritol, contains four hydroxyl groups and accordingly can be used). Suitable five hydroxyl group-containing monosaccharides are galactose, fructose, and sorbose. Sugar alcohols containing six -OH groups derived from the hydrolysis products of sucrose, as well as glucose and sorbose, e.g., sorbitol, are also suitable. Examples of disaccharide polyols which can be used include maltose, lactose, and sucrose, all of which contain eight hydroxyl groups.

Preferred polyols for preparing the polyesters for use in the present invention are selected from the group consisting of erythritol, xylitol, sorbitol, glucose and sucrose. Sucrose is especially preferred.

The polyol starting material having at least four hydroxyl groups must be esterified on at least four of the -OH groups with a fatty acid containing from about 8 to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers, depending on the desired physical properties (e.g., liquid of a desired viscosity or solid) of the polyol fatty acid polyester compound being prepared.

Fatty acids per se or naturally occurring fats and oils can serve as the source for the fatty acid component in the polyol fatty acid polyester. For example, rapeseed oil provides a good source of $C_{22}$ fatty acids. The $C_{16}$-$C_{18}$ fatty acids can be obtained from tallow, soybean oil, and cottonseed oil. Shorter chain fatty acids can be obtained from coconut, palm kernel, and babassu oils. Corn oil, lard, oil, palm oil, peanut oil, safflower seed oil, sesame seed oil, and sunflower seed oil are examples of other natural oils which can serve as the source of the fatty acid used to prepare the polyesters herein.

Preferred fatty acids for preparing the polyol polyesters herein are the $C_{14}$ to $C_{18}$ acids, and are most preferably selected from the group consisting of myristic, palmitic, stearic, oleic, and linoleic fatty acids. Thus, natural fats and oils which have a high content of these fatty acids represent preferred sources for the fatty acid component, i.e., soybean oil, olive oil, cottenseed oil, corn oil, tallow and lard.

The polyol fatty acid polyesters useful in this invention must contain at least four fatty acid ester groups. Polyol fatty acid polyester compounds that contain three or less fatty acid ester groups are digested in and the products of digestion are absorbed from the intestinal tract much in the manner of ordinary triglyceride fats, whereas the polyol fatty acid polyester compounds that contain four or more fatty acid ester groups are substantially non-digestible and consequently nonabsorbable by the human body. It is not necessary that all of the hydroxyl groups of the polyol be esterified with fatty acid, but it is preferable that the polyester contain no more than two unesterified hydroxyl groups. Most preferably, substantially all of the hydroxyl groups of the polyol are esterified with fatty acid, i.e., the compound is substantially completely esterified. The fatty acids esterified to the polyol molecule can be the same or mixed.

To illustrate the above points, a sucrose fatty triester would not be suitable for use herein because it does not contain the required four fatty acid ester groups. A sucrose tetra-fatty acid ester would be suitable, but is not preferred because it has more than two unesterified hydroxyl groups. A sucrose hexa-fatty acid ester would be preferred because it has no more than two unesterified hydroxyl groups. Highly preferred compounds in which all the hydroxyl groups are esterified with fatty acid include the sucrose octa-fatty acid esters.

In any given polyol fatty acid polyester compound the fatty acid ester groups can be selected on the basis of the desired physical properties of the compound. For example, the polyol polyesters which contain unsaturated fatty acid ester groups and/or a preponderance of short chain, e.g., $C_{12}$, fatty acid ester groups are generally liquid at room temperature. The polyols esterified with longer chain and/or saturated fatty acid groups such as stearoyl are solids at room temperatures.

The following are non-limiting examples of specific polyol fatty acid polyesters containing at least four fatty acid ester groups suitable for use in the present invention: glucose tetraoleate, glucose tetrastearate, the glucose tetraesters of soybean oil fatty acids, the mannose tetraesters of mixed tallow fatty acids, the galactose tetraesters of olive oil fatty acids, the arabinose tetraesters of cottonseed oil fatty acids, xylose tetralinoleate, galactose pentastearate, sorbitol tetraoleate, the sorbitol hexaesters of olive oil fatty acids, xylitol pentapalmitate, the xylitol tetraesters of substantially completely hydrogenated cottonseed oil fatty acids, sucrose tetrastearate, sucrose pentastearate, sucrose hexaoleate, sucrose octaoleate, the sucrose octaesters of partially or substantially completely hydrogenated soybean oil fatty acids and the sucrose octaesters of peanut oil fatty acids.

As noted above, highly preferred polyol fatty acid esters are those wherein the fatty acids contain from about 14 to about 18 carbon atoms and are thus derived from such natural materials as soybean oil and olive oil. Examples of such compounds are the erythritol tetraesters of olive oil fatty acids, erythritol tetraoleate, xylitol pentaoleate, sorbitol hexaoleate, sucrose octaoleate, and the sucrose hexa-, hepta- and octaesters of soybean oil fatty acids, partially or substantially wholly hydrogenated.

The polyol fatty acid polyesters suitable for use herein can be prepared by a variety of methods well known to those skilled in the art. These methods include: tranesterification of the polyol with methyl, ethyl or glycerol fatty acid esters using a variety of cataysts; acylation of the polyol with a fatty acid chloride; acylation of the polyol with a fatty acid anhydride; and acylation of the polyol with a fatty acid, per se. As an example, the preparation of polyol fatty acid esters is described in U.S. Pat. No. 2,831,854, incorporated herein by reference.

Specific, but non-limiting, examples of the preparation of polyol fatty acid esters suitable for use in the practice of this invention are as follows.

Erythritol tetraoleate — Erythritol and a five-fold molar excess of methyl oleate are heated at 180° C, under vacuum, with agitation, in the presence of sodium methoxide catalyst over two reaction periods of several hours each. The reaction product (predominately erythritol tetraoleate) is refined in petroleum ether and crystallized three times from several volumes of acetone at 1° C.

Xylitol pentaoleate — Xylitol and a five-fold molar excess of methyl oleate in dimethylacetamide (DMAC) solution are heated at 180° C for five hours in the presence of sodium methoxide catalyst, under vacuum. During this time the DMAC is removed by distillation. The product (predominately xylitol pentaoleate) is refined in petroleum ether solution and, after being freed of petroleum ether, is separated as a liquid layer four times from acetone at ca. 1° C and twice from alcohol at ca. 10° C.

Sorbitol hexaoleate is prepared by essentially the same procedure used to prepare xylitol pentaoleate except that sorbitol is substituted for xylitol.

Sucrose octaoleate is prepared by substantially the same procedure as that used to prepare erythritol tetraoleate except that sucrose is substituted for erythritol.

The SPE material used in the animal studies described hereinabove was a preferred, purified reaction product which primarily comprised a mixture of sucrose hexa-, hepta-, and octa-esters (avg. ca. 7.5 ester groups per molecule), prepared from mixed $C_{14}$-$C_{18}$ fatty acids.

The vitamins used to fortify the foregoing polyesters are described in detail hereinafter. It will be appreciated that commercial preparations of the appropriate vitamins and/or appropriate vitamin mixtures which provide vitamins A, D, E and K can be used herein.

In general terms, the vitamins are classified as either "fat-soluble" or "water-soluble". The fat-soluble vitamins are used to fortify the polyester materials herein. The fat-soluble vitamins include vitamin A, vitamin D, vitamin E, and vitamin K.

Vitamin A (retinol) can be used to fortify the polyesters herein. Vitamin A is a fat-soluble alcohol of the formula $C_{20}H_{29}OH$. Natural vitamin A is usually found esterified with a fatty acid; metabolically active forms of vitamin A also include the corresponding aldehyde and acid. All such fat-soluble forms of vitamin A (including the carotenoids) are contemplated for use in the present invention and are considered to be encompassed by the term "vitamin A" as used herein. The role of vitamin A in normal human metabolism has not been established with certainty, but it is known that this vitamin is essential to proper vision.

Vitamin D (calciferol) can be used to fortify the polyesters herein. Vitamin D is a fat-soluble vitamin well known for use in the treatment and prevention of rickets and other skeletal disorders. "Vitamin D" comprises sterols, and there are at least 11 sterols with vitamin D-type activity. Of these, only those known as $D_2$ and $D_3$ are of substantial practical importance. Ergosterol, a plant sterol closely related to cholesterol in structure, is known as "provitamin $D_{22}$" and 7-dehydrocholesterol is known as "provitamin $D_3$". Each of these provitamins is converted to the corresponding active form by irradiation with ultraviolet light. Ergocalciferol ($D_2$) is prepared commercially for use as a vitamin supplement. Cholecalciferol ($D_3$) is a form synthesized in animal tissues and is chiefly found in the natural fish oils. The present invention fully contemplates the use of any of the vitamins and provitamins having "vitamin D-type" activity and the term "vitamin D" as used herein is intended to encompass all such fat-soluble materials.

Vitamin E (tocopherol) is a third fat-soluble vitamin which can be used in the present invention. Four different tocopherols have been identified (alpha, beta, gamma and delta), all of which are oily, yellow liquids, insoluble in water but soluble in fats and oils. Of the four tocopherols, alpha is the most active biologically, a factor which may be related to better absorption from the intestine. Delta tocopherol is the most potent antioxidant of the four. It has been suggested that vitamin E deficiency may cause a variety of symptoms such as fetal abnormalities and deaths, myocardial degeneration, and necrosis of the liver, but the role of this vitamin in human nutrition is not yet well established. The term "vitamin E" as employed herein is intended to encompass all the fat-soluble tocorpherols having "vitamin- E-type" activity.

Vitamin K exists in at least three forms, all belonging to the group of chemical compounds known as quinones. The naturally-occurring fat-soluble vitamins are $K_1$ (phylloquinone), $K_2$ (menaquinone), and $K_3$ (menadione). Vitamin K deficiency usually results in poor clotting of the blood, among other symptons. The term "vitamin K" as employed herein is intended to include all the foregoing fat-soluble quinones having "vitamin K-type" activity.

From the foregoing it is to be understood that vitamins A, D, E and K, the corresponding provitamins and derivatives thereof, such as esters, having vitamin A, D, E or K-type activity in animals, especially humans, are fully contemplated for use herein and are encompassed by the term "vitamin" as used herein.

The amount of the individual fat-soluble vitamins used to fortify the present compositions can vary with the age of the recipient, the dosage regimen used, and the amount of the vitamin ingested from other dietary sources. For example, in younger, growing children or in pregnant females it is recognized that larger amounts of any given vitamin should be ingested to supply optimal nutritional benefits than are needed with adult males. If the user of the present compositions happens to ingest foods which are extremely rich in a given fat-soluble vitamin, less of that vitamin need be used in the present compositions to insure adequate intestinal uptake for good nutrition. In any event, an attending physician can, if so desired, measure the amount of fat-soluble vitamins in the plasma. Based on these data, the appropriate type and amount of fat-soluble vitamin used to fortify the polyesters herein can then be determined on an individual basis.

More simply, the formulator of the compositions herein can fortify the polyesters with a recommended daily allowance (RDA), or increment or multiple of an RDA, of any of the fat-soluble vitamins to insure that the user of the compositions will maintain a nutritionally adequate uptake of said vitamins. For example, with vitamin A a daily amount in the range of 20 international units (I.U.) to about 57 I.U. per kilogram of body weight can be employed. With vitamin D, fortification of the compositions to provide about 400 I.U., total, per day is ample. When supplementing with vitamin E, the amount of the vitamin optimal for dietary intake ranges from 3-6 I.U. for infants to 25-30 I.U., total, per day, for adults. When supplementing with vitamin K, it is more difficult to estimate the amount to be ingested to provide adequate nutrition since the microorganisms living in the intestine can synthesize this vitamin. However, it is known that ingestion of from 0.5 mg.-1 mg. of vitamin K per day will prevent insufficiency.

As can be seen from the foregoing, the amount of the fat-soluble vitamins employed herein to fortify the polyesters can vary. In general, the polyesters are fortified with sufficient fat-soluble vitamin to provide from about 0.08% to about 150% of the average RDA. Compositions comprising from about 98% to about 99.999% by weight of the polyesters herein and from about 0.001% to about 2% by weight of vitamin A, D, E, and K, or mixtures thereof, are easily prepared and used both in foods and in pharmaceutical compositions. Higher or lower concentrations of the vitamins can be used, according to the desires of the formulator and the dietary needs of the user. Preferred compositions comprise from about 99.0% to about 99.99% by weight of the polyester and from about 0.01% to about 1.0% by weight of the fat-soluble vitamins. The desired amount of the vitamins is simply dissolved in the polyesters.

In the therapeutic regimens of this invention the dosage of the vitamin-fortified polyester will vary with the severity of the hypercholesterolemic condition and the duration of the treatment. Dosages can range from about 0.01 mg./kg. to about 500 mg./kg. (unless otherwise specified, the unit designated "mg./kg." as used herein refers to mg. of polyester per kilogram of body weight), preferably from about 0.1 mg./kg. to about 125 mg./kg. with up to six dosages, preferably three dosages, daily. Individual dosages greater than about 500 mg./kg. or daily dosages greater than about 1,000 mg./kg., although effective, may produce laxative effects. Dosages of less than about 0.1 mg./kg. do not materially inhibit the absorption of cholesterol in most patients. Most preferably, the polyesters are administered at meal times. The dosages can be administered orally in any suitable unit dosage form such as pills, tablets, and capsules. Preferred are capsules made from gelatin.

The pharmaceutical compositions herein can comprise the vitamin-fortified polyester, alone, or in combination with any desired, non-interfering pharmaceutical carrier. As used herein, the term "pharmaceutical carrier" means a solid or liquid filler, diluent or encapsulating substance. Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate, powdered tragacanth; malt; gelatin; talc; oils, such as peanut oil, cottonseed oil, sesame oil, olive oil, corn oil and soybean oil; polyols such as propylene glycol, glycerin, sorbitol, mannitol, and polyethylene glycol; agar; alginic acid; pyrogen-free water; isotonic saline; ethyl alcohol and phosphate buffer solutions, as well as other non-toxic compatible substances used in pharmaceutical formulations. Wetting agents and lubricants such as sodium lauryl sulfate, as well as coloring agents, flavoring agents and preservatives, can also be present in the compositions, according to the desires of the formulator.

The pharmaceutical carriers of the foregoing type can optionally be employed in conjunction with the vitamin-fortified polyesters herein to provide a practical size to dosage relationship, composition forms which can be easily ingested, and means for providing accurate unit dosages in a convenient form. The pharmaceutical carrier can comprise from about 0.1% to 99% by weight of the total pharmaceutical composition.

The vitamin-fortified sugar (or sugar alcohol) fatty acid polyesters of the present invention can be used as a partial or total replacement for normal triglyceride fats in any fat-containing food compositiion to provide anti-hypercholesterolemic and low calorie benefits. In order to achieve these benefits in a reasonable time, it is necessary that at least about 10% of the fat in the food composition comprises the polyesters herein. Highly desirable food compositions are those wherein the fat component is replaced by up to about 100% of the vitamin-fortified polyesters herein. Hence, the vitamin-fortified polyesters of this invention can be used as a partial or complete replacement for normal triglyceride fats in a salad or cooking oil, or in plastic shortenings for use in frying, cake making, bread making, and the like. The vitamin-fortified polyesters can also be used as partial or complete replacements for normal triglyceride fats in fat-containing food products such as mayonnaise, margarine, and dairy products.

Preferred fat-containing food compositions of the present type comprise non-fat ingredients and fat ingredients wherein from about 10% to about 100% of the total fat consists essentially of a sugar fatty acid polyester having at least four fatty acid ester groups, each fatty acid having from about 8 to about 22 carbon atoms, said sugar fatty acid polyester and/or food composition made therefrom being fortified with a fat-soluble vitamin in the manner disclosed herein. The most highly preferred food compositions are those wherein the sugar fatty acid ester contains no more than two unesterified hydroxyl groups. Sucrose polyesters, especially those wherein the ester groups contain 14 to 18 carbon atoms, when used in the manner of this invention, are especially preferred for use in vitaminized anti-hypercholesterolemic and low calorie food compositions.

The following, non-limiting examples illustrate the compositions and processes of this invention. It will be appreciated that sugars and sugar alcohols, appropriately esterified, are encompassed by the term "sugar" as used herein and such materials can be interchanged in the compositions.

EXAMPLE I

Gelatin capsules comprising a vitamin-fortified polyester are prepared by conventional methods, as follows:

| Ingredient | Amount per Capsule |
|---|---|
| Sucrose polyester* | 1500 mg. |
| Retinol | 0.3 RDA |
| Starch | 20 mg. |
| Sodium laurylsulfate | 2.9 mg. |

*Mixed hexa-, hepta- and octa-sucrose esters, predominately the octa-ester, esterified with mixed soybean oil fatty acids, predominately in the $C_{16}$-$C_{18}$ chain length.

The capsules of the foregoing type are administered orally three times daily (two with each meal). This treatment regimen inhibits cholesterol uptake significantly and decreases the serum cholesterol levels in the circulatory systems of humans with, or disposed towards, hyperchlolesterolemia. Vitamin A levels in the patients are not decreased significantly from the normal.

Similar results are obtained when the sucrose polyester in the capsules of Example I is replaced with an equivalent quantity of a fatty acid polyester selected from the group consisting of glucose tetraoleate; glucose tetrastearate; mixed glucose tetraesters of soybean oil fatty acids; mixed mannose tetraesters of tallow fatty acids; mixed galactose tetraesters of olive oil fatty acids; mixed arabinose tetraesters of cottonseed oil fatty acids; xylose tetralinoleate; galactose pentastearate; sorbitol tetraoleate; sucrose tetrastearate; sucrose pentastearate; sucrose hexaoleate; sucrose heptaoleate; and sucrose octaoleate, respectively.

In the composition of Example I the retinol is replaced by an equivalent dosage level of a commercial vitamin A ester concentrate and equivalent results are secured.

EXAMPLE II

Gelatin capsules comprising a unit dosage form of a polyester and vitamin E are prepared by conventional means, as follows:

| Ingredient | Amount per Capsule |
|---|---|
| Sucrose octaoleate | 3500 mg. |
| Vitamin E* | 0.2 RDA |
| Starch | 25 mg. |

*Consists of mixed alpha, beta, gamma and delta tocopherols.

The above capsules are administered orally three times daily (three per meal/70 kg. man) over a one-month period. This treatment regimen substantially inhibits cholesterol uptake in the patient and decreases the serum level of cholesterol. No vitamin E deficiency in the patient is noted.

The capsules of Example II are additionally supplemented with sufficient β-carotene to provide a 0.25 RDA of vitamin A per capsule.

EXAMPLE III

Gelatin capsules comprising a polyester and containing a mixture of the fat-soluble vitamins is as follows:

| Ingredient | Mg. per Capsule |
|---|---|
| Sucrose octaoleate | 1500 |
| Vitamin A | 0.1 |
| Vitamin D | 0.01 |
| Vitamin E | 0.1 |
| Vitamin K | 0.1 |

The vitamin A employed in the capsules of Example III is retinol; the vitamin D is a 1:1 mixture of irradiated ergosterol and irradiated 7-dehydrocholesterol; the vitamin E comprises a commercial mixture of alpha, beta, gamma and delta tocopherols; and the vitamin K comprises the fat-soluble phylloquinone.

Capsules of the type prepared in Example III administered orally three times daily (two with each meal) substantially inhibit cholesterol uptake and decrease the level of cholesterol in the circulatory system of a 70 kg. patient afflicted with hypercholesterolemia. The body levels of fat-soluble vitamins A, D, E and K do not decrese below normal.

EXAMPLE IV

A low calorie, fat-containing salad oil suitable for use by a patient on an anti-hypercholesterolemia and anti-hyperlipidemia diet is as follows:

| Ingredient | % by Weight |
|---|---|
| Soybean oil* | 50 |
| Vitaminized sucrose polyester** | 50 |

*Refined, bleached and lightly hydrogenated oil.
**Avg. 7.5 ester of sucrose and mixed soybean oil fatty acids fortified to provide 1000 I.U. of vitamin A per one ounce serving.

The composition of the foregoing type is suitable for use in standard fashion as a liquid salad oil. The continued use of the oil as a replacement for regular salad oil lowers the body's cholesterol level but does not cause depletion of vitamin A in the tissues.

EXAMPLE V

A plastic shortening is prepared from the following ingredients.

| Ingredient | % by Weight |
|---|---|
| Soybean oil* | 50 |
| Vitaminized xylitol pentaoleate** | 40 |
| Tristearin | 10 |

*Lightly hydrogenated oil, iodine value 107.
**Vitaminized with sufficient irradiated ergosterol to provide 40.0 I.U. of vitamin D per two ounce serving.

The composition of Example V is prepared by thoroughly mixing the indicated ingredients. The composition is suitable for use in frying and other types of cooking where a plastic fat is employed. The fat composition of Example V can also be employed in the preparation of baking doughs suitable for use by the hypercholesterolemic patient. Continued ingestion of the plastic shortening of Example V, or foods made therefrom, reduces the body's serum cholesterol level and does not result in vitamin D deficiency.

The shortening of Example V can be used by the normal or hyperlipidemic patient to control obesity.

EXAMPLE VI

A vitamin-fortified margarine composition is as follows.

| Ingredient | % by Weight |
|---|---|
| Vitaminized sucrose octaoleate* | 80 |
| Milk solids | 2 |
| Salt | 2 |
| Monoglyceride | 15 |
| Water | 1 |

*Vitamin-fortified with a commercial mixture of vitamins A, D, E and K sufficient to provide an RDA of each of these vitamins per three ounce serving of margarine.

The margarine of Example VI is prepared by simply combining the ingredients. The mrgarine can be colored, if desired, with standard food colors. The margarine is suitable for use by the hypercholesterolemic patient to reduce serum cholesterol levels while maintaining normal levels of the fat-soluble vitamins.

The margarine of Example VI can be used by the normal or hyperlipidemic patient to control obesity.

The polyesters herein are also useful by virtue of their stool-softening effect. Accordingly, when vitamin-fortified in the manner of this invention, the polyesters can be used as laxatives and are preferred over mineral oil for this use since the polyesters are not undesirably deposited in the liver.

EXAMPLE VII

A stool-softening laxative is as follows.

| Ingredient | % by Weight |
| --- | --- |
| Vitaminized sucrose polyester* | 99.5 |
| Oil of peppermint (flavor) | 0.5 |

*Liquid avg. 7.5 ester of sucrose/mixed soybean oil fatty acids fortified with a commercial mixture of vitamins A, D, E and K sufficient to provide an RDA of each of these vitamins per 30 gram dose of laxative.

The composition of Example VII is prepared by simply mixing the indicated ingredients. In use, 10–15 grams of the composition is ingested once or twice daily to provide a stool-softening effect. More or less of the composition can be used, according to need.

The composition of Example VII is ingested at the rate of ca. 5–7 grams four to six times daily to reduce serum cholesterol levels.

As can be seen from the foregoing, the vitamin-fortified polyester compositions herein are useful in low calorie diets, as pharmaceutical compositions for treating hypercholesterolemic patients and as laxatives. The degree to which the compositions are fortified with the vitamins can vary according to good nutritional practice such that the body's stores of the fat-soluble vitamins are not substantially interfered with. It will be understood by the physician or nutritionist that the amount of a given fat-soluble vitamin with which to fortify the instant compositions can be varied according to the needs of the individual patient. The formulator of compositions of the present type will appreciate that compositions for general use can be prepared by dissolving a sufficient quantity of any of the fat-soluble vitamins, or mixtures thereof, in the polyesters to provide from about 0.1 RDA to about 1.0 RDA, or more, of said vitamins per total daily dose of said compositions. In this way, the desired anti-hypercholesterolemic and/or anti-hyperlipidemic effect can be secured without fear of avitaminosis or hypervitaminosis when the compositions are properly used.

Highly preferred compositions herein are those wherein the polyester materials comprise the $C_{14}$, $C_{16}$ and $C_{18}$ hexa-, hepta-, and octa-esters of sucrose. Sucrose hexaoleate, heptaoleate, octaoleate, and mixtures thereof, are bland, easily prepared, toxicologically acceptable, and preferred for use herein, especially in combinaton with vitamins A and E.

What is claimed is:

1. A composition of matter, comprising: a non-absorbable, non-digestible polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and sufficient fat-soluble vitamin selected from the group consisting of vitamin A, vitamin D, vitamin E and vitamin K, or mixtures thereof, to prevent abnormally low levels of any of said fat-soluble vitamins in animals ingesting said composition.

2. A composition according to claim 1 wherein the polyol fatty acid polyester contains no more than 2 free hydroxyl groups.

3. A composition according to claim 2 wherein the fatty acid ester groups contain from about 14 to about 18 carbon atoms.

4. A composition according to claim 3 wherein the polyol is a member selected from the group consisting of erythritol, xylitol, sorbitol, glucose and sucrose.

5. A composition according to claim 4 wherein the polyol is sucrose.

6. A composition according to claim 5 wherein the sucrose fatty acid polyester is a member selected from the group consisting of $C_{14}$, $C_{16}$ and $C_{18}$ hexa-, hepta-, and octa-esters, and mixtures thereof.

7. A composition according to claim 6 wherein the sucrose fatty acid polyester is a member selected from the group consisting of the hexaoleate, heptaoleate and octaoleate of sucrose, and mixtures thereof.

8. A composition according to claim 1 which comprises from about 98% to about 99.999% by weight of the non-absorbable, non-digestible polyol fatty acid polyester and from about 0.001% to about 2% by weight of a vitamin selected from the group consisting of vitamin A, vitamin D, vitamin E, vitamin K, and mixtures thereof.

9. A pharmaceutical composition in effective unit dosage amounts for inhibiting the absorption of cholesterol without interfering with the body's stores of fat-soluble vitamins, comprising: from about 0.1 gram to about 5 grams of a non-absorbable, non-digestible polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and sufficient fat-soluble vitamin selected from the group consisting of vitamin A, vitamin D, vitamin E and vitamin K, or mixtures thereof, to prevent abnormally low levels of any of said fat-soluble vitamins in humans ingesting said composition.

10. A composition according to claim 9 wherein the polyol fatty acid polyester contains no more than 2 free hydroxyl groups.

11. A composition according to claim 10 wherein the fatty acid ester groups contain from about 14 to about 18 carbon atoms.

12. A composition according to claim 11 wherein the polyol is a member selected from the group consisting of erythritol, xylitol, sorbitol, glucose and sucrose.

13. A composition according to claim 12 wherein the polyol is sucrose.

14. A composition according to claim 13 wherein the sucrose fatty acid polyester is a member selected from the group consisting of $C_{14}$, $C_{16}$ and $C_{18}$ hexa-, hepta-, and octa-esters, and mixtures thereof.

15. A composition according to claim 14 wherein the sucrose fatty acid polyester is a member selected from the group consisting of the hexaoleate, heptaoleate and octaoleate of sucrose, and mixtures thereof.

16. A low calorie fat-containing food composition comprising non-fat ingredients and fat ingredients wherein from about 10% to about 100% of the total fat ingredients comprise a non-absorbable, non-digestible polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms, said food composition being fortified with sufficient fat-soluble vitamin selected from the group consisting of vitamin A, vitamin D, vitamin E and vitamin K, or mixtures thereof, over and above that naturally present in said food composition, to prevent abnormally low levels of any of said fat-soluble vitamins in animals ingesting said composition.

17. A composition according to claim 16 wherein the polyol fatty acid polyester contains no more than 2 free hydroxyl groups.

18. A composition according to claim 17 wherein the fatty acid ester groups contain from about 14 to about 18 carbon atoms.

19. A composition according to claim 18 wherein the polyol is a member selected from the group consisting of erythritol, xylitol, sorbitol, glucose and sucrose.

20. A composition according to claim 19 wherein the polyol is sucrose.

21. A composition according to claim 20 wherein the sucrose fatty acid polyester is a member selected from the group consisting of $C_{14}$, $C_{16}$ and $C_{18}$ hexa-, hepta-, and octa-esters, and mixtures thereof.

22. A composition according to claim 21 wherein the sucrose fatty acid polyester is a member selected from the group consisting of the hexaoleate, heptaoleate and octaoleate of sucrose, and mixtures thereof.

23. A method for inhibiting the absorption of cholesterol without decreasing the body's stores of fat-soluble vitamins comprising systemically administering to an animal susceptible to or afflicted with hypercholesterolemia successive therapeutically effective doses of a non-absorbable and non-digestible polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms and sufficient fat-soluble vitamin to prevent abnormally low levels of said vitamin from developing in said animal.

* * * * *